(12) United States Patent
Borkholder et al.

(10) Patent No.: US 11,622,730 B2
(45) Date of Patent: Apr. 11, 2023

(54) PULSE WAVE VELOCITY, ARTERIAL COMPLIANCE, AND BLOOD PRESSURE

(71) Applicants: David A. Borkholder, Canandaigua, NY (US); Alexander S. Liberson, Pittsford, NY (US); Jeffrey S. Lillie, Mendon, NY (US); Steven W. Day, Rochester, NY (US)

(72) Inventors: David A. Borkholder, Canandaigua, NY (US); Alexander S. Liberson, Pittsford, NY (US); Jeffrey S. Lillie, Mendon, NY (US); Steven W. Day, Rochester, NY (US)

(73) Assignee: Rochester Institute of Technology, Rochester, NY (US)

( * ) Notice: Subject to any disclaimer, the term of this patent is extended or adjusted under 35 U.S.C. 154(b) by 989 days.

(21) Appl. No.: 15/527,412

(22) PCT Filed: Nov. 17, 2015

(86) PCT No.: PCT/US2015/061188
§ 371 (c)(1),
(2) Date: May 17, 2017

(87) PCT Pub. No.: WO2016/081517
PCT Pub. Date: May 26, 2016

(65) Prior Publication Data
US 2019/0083045 A1    Mar. 21, 2019

Related U.S. Application Data

(60) Provisional application No. 62/080,738, filed on Nov. 17, 2014, provisional application No. 62/080,740, filed on Nov. 17, 2014.

(51) Int. Cl.
*A61B 5/00* (2006.01)
*A61B 5/02* (2006.01)
(Continued)

(52) U.S. Cl.
CPC ............ *A61B 5/7278* (2013.01); *A61B 5/021* (2013.01); *A61B 5/02007* (2013.01);
(Continued)

(58) Field of Classification Search
None
See application file for complete search history.

(56) References Cited

U.S. PATENT DOCUMENTS 2,658,505 A  *  11/1953  Sheer ................... A61B 5/0285
                                                       600/500
4,799,491 A       1/1989  Eckerle
(Continued)

FOREIGN PATENT DOCUMENTS

JP    2014-100249 A    6/2014
WO    01/78599 A2      10/2001
(Continued)

OTHER PUBLICATIONS

Babbs, Charles F. "Noninvasive measurement of cardiac stroke volume using pulse wave velocity and aortic dimensions: a simulation study." Biomedical engineering online 13.1 (2014): 137. (Year: 2014).*
(Continued)

*Primary Examiner* — Jacqueline Cheng
*Assistant Examiner* — Jairo H Portillo
(74) *Attorney, Agent, or Firm* — Bond Schoeneck & King, PLLC; Joseph M. Noto

(57) ABSTRACT

Disclosed are methods for determining physiological parameters of an individual including blood pressure, arterial compliance, flow velocity, and pressure wave velocity. A noninvasive method for determining the blood pressure of a patient is based on measurements of flow velocity, pulse wave velocity and arterial compliance. A noninvasive method for determining the arterial compliance of a patient
(Continued)

is based on measurements of blood pressure, flow velocity, and pulse wave velocity.

20 Claims, 6 Drawing Sheets

(51) Int. Cl.
| | | |
|---|---|---|
| *G09B 23/28* | (2006.01) | |
| *G09B 23/30* | (2006.01) | |
| *A61B 5/0285* | (2006.01) | |
| *A61B 5/021* | (2006.01) | |
| *A61B 5/0295* | (2006.01) | |
| *A61B 5/352* | (2021.01) | |

(52) U.S. Cl.
CPC ........ *A61B 5/0285* (2013.01); *A61B 5/02125* (2013.01); *G09B 23/28* (2013.01); *G09B 23/288* (2013.01); *G09B 23/30* (2013.01); *A61B 5/0295* (2013.01); *A61B 5/352* (2021.01)

(56) References Cited

U.S. PATENT DOCUMENTS

| | | | |
|---|---|---|---|
| 5,309,916 A | 5/1994 | Hatschek | |
| 5,687,731 A | 11/1997 | Ragozin et al. | |
| 5,743,856 A | 4/1998 | Oka et al. | |
| 6,113,543 A * | 9/2000 | Bonnefous | A61B 5/02007 600/438 |
| 6,413,223 B1 | 7/2002 | Yang et al. | |
| 6,537,225 B1 * | 3/2003 | Mills | A61B 5/02028 600/323 |
| 6,599,251 B2 | 7/2003 | Chen et al. | |
| 6,736,789 B1 | 5/2004 | Spickerman et al. | |
| 6,984,207 B1 * | 1/2006 | Sullivan | A61B 5/0002 600/300 |
| 7,621,876 B2 | 11/2009 | Hoctor et al. | |
| 7,672,706 B2 | 3/2010 | Sathyanarayana | |
| 7,674,231 B2 | 3/2010 | McCombie et al. | |
| 9,011,346 B2 | 4/2015 | Wiard et al. | |
| 2002/0183629 A1 | 12/2002 | Fitz | |
| 2003/0095695 A1 | 5/2003 | Arnold | |
| 2003/0135124 A1 | 7/2003 | Russell | |
| 2004/0088123 A1 | 5/2004 | Ji | |
| 2005/0107710 A1 | 5/2005 | Nakayama | |
| 2005/0124892 A1 | 6/2005 | Weitzel et al. | |
| 2005/0228296 A1 | 10/2005 | Banet | |
| 2008/0108930 A1 | 5/2008 | Weitzel et al. | |
| 2010/0081946 A1 | 4/2010 | Garudadri et al. | |
| 2010/0105901 A1 | 4/2010 | Fujita et al. | |
| 2010/0106016 A1 * | 4/2010 | Orbay | A61B 5/021 600/437 |
| 2010/0241011 A1 * | 9/2010 | McCombie | A61B 5/02125 600/485 |
| 2011/0172505 A1 | 7/2011 | Kim et al. | |
| 2011/0295579 A1 | 12/2011 | Tang et al. | |
| 2012/0215117 A1 * | 8/2012 | Karst | A61N 1/36585 600/486 |
| 2013/0046192 A1 | 2/2013 | Lin et al. | |
| 2013/0109982 A1 | 5/2013 | Sato et al. | |
| 2013/0172691 A1 | 7/2013 | Tran | |
| 2013/0331678 A1 * | 12/2013 | Lading | A61B 5/1075 600/393 |
| 2014/0296677 A1 | 10/2014 | McEowen | |
| 2015/0112158 A1 | 4/2015 | He et al. | |
| 2015/0112606 A1 | 4/2015 | He et al. | |
| 2015/0164351 A1 | 6/2015 | He et al. | |
| 2015/0245776 A1 | 9/2015 | Hirohata et al. | |
| 2017/0354331 A1 | 12/2017 | Borkholder et al. | |

FOREIGN PATENT DOCUMENTS

| | | |
|---|---|---|
| WO | 2007067690 | 6/2007 |
| WO | 2010018542 | 2/2010 |
| WO | 2010020914 A1 | 2/2010 |
| WO | 2013110929 A1 | 8/2013 |
| WO | 2014074901 A1 | 5/2014 |
| WO | WO 2014/077233 A1 | 5/2014 |

OTHER PUBLICATIONS

Lee, Vivian S., et al. "Flow quantification using fast cine phase-contrast MR imaging, conventional cine phase-contrast MR imaging, and Doppler sonography: in vitro and in vivo validation. "nbsp;AJR. American journal of roentgenology 169.4 (1997): 1125-1131. (Year: 1997).*
Chen, Yan. Continuous and noninvasive blood pressure measurement by pulse wave velocity: a new and systematic modeling methodology. Diss. 2012. (Year: 2012).*
Supplementary European Search Report, International Application No. EP 15 86 0209, pp. 1-9, dated Jun. 11, 2018.
Misra et al. "A study of solitary waves in a tapered aorta by using the theory of solitons". Computers and Mathematics with Applications, Elsevier, Amsterdam, NL. vol 54, No. 2. Jun. 8, 2007. pp. 242-254.
"Nonlinear Waves in Fluid Flow through a Viscoelastic Tube", Fluid Dynamics, 2006, pp. 49-62, vol. 41, No. 1.
"Continuous Blood Pressure Measurement by using the Pulse Transit Time: Comparison to a Cuff-based Method", Eur J Appl Physiol, DOI 10.1007/s00421-011-1983-3.
"Pulse Wave Propagation in a model human arterial network: Assessment of 1-D visco-elastic simulations against in vitro measurements", J Biomech, Aug. 11, 2011, pp. 2250-2258, DOI:10.1016/j.jbiomech.2011.05.041.
"Estimation of Arterial Nonlinear Compliance using Ultrasound Images", Electronics and Electrical Engineering, 2010, ISSN 1392-1215, No. 9(105).
"Continuous Blood Pressure Monitoring During Exercise Using Pulse Wave Transit Time Measurement" DOI:0-7803-8439-3/04/.
"Continuous Estimation of Systolic Blood Pressure using the Pulse Arrival Time and Intermittent Calibration" Med. Biol. Eng. Comput, 2000, pp. 569-574, vol. 38.
"The Relationship Between Modified Pulse Wave Transit Time and Cardiovascular Changes in Isoflurane Anesthetized Dogs", Journal of Clinical Monitoring and Computing 15, 1999, pp. 493-501.
"Left Ventricular Ejection Time: a Potential Determinant of Pulse Wave Velocity in Young, Healthy Males", DOI: 10.1097/01.hjh.0000098125.00558.40.
"Left Ventricular Ejection Time, Not Heart Rate, is an Independent Correlate of Aortic Pulse Wave Velocity", DOI:10.1152/japplphysiol.00475.2013.
"Pulse Rate Transit Time Measured from the ECG: an Unreliable Marker of Beat to Beat Blood Pressure", DOIL10.1152/japplphysiol.00657.2005.
International Search Report Form PCT/ISA/220, International Application No. PCT/US2015/061188, pp. 1-9, dated Jun. 9, 2016.
Non-Final Office Action dated Aug. 5, 2019 for U.S. Appl. No. 15/527,467, 14 pages.
Final Office Action dated Apr. 15, 2020 for U.S. Appl. No. 15/527,467, 23 pages.
Non-Final Office Action dated Feb. 16, 2021 for U.S. Appl. No. 15/527,467, 18 pages.
Non-Final Office Action dated Oct. 29, 2021 for U.S. Appl. No. 15/527,467, 20 pages.
Examination Report dated Apr. 13, 2021 for European Application No. 15861809.0, 9 pages.
International Search Report and Written Opinion dated Mar. 2, 2016 for International Application No. PCT/US2015/061190, 7 pages.
Extended European Search Report dated Jun. 27, 2018 for European Application No. 15860209.4, 7 pages.
Examination Report dated Apr. 13, 2021 for European Application No. 15860209.4, 9 pages.
Gasser, T. C. et al., "Hyperrealistic modelling of arterial layers with distributed collagen fibre orientations," Journal of the Royal Society Interface, 3(6):15-35 (2005).

(56) References Cited

OTHER PUBLICATIONS

Holzapfel, G. A. et al., "Constitutive modelling of arteries," Proceedings of The Royal Society of London, 466(2118):1551-1597 (2010).

Konig, G. et al., "Mechanical properties of completely autologous human tissue engineered blood vessels compared to human saphenous vein and mammary artery," Biomaterials, 30(8):1542-1550 (2009).

O'Rourke, M., "Arterial stiffness, systolic blood pressure, and logical treatment of arterial hypertension," Hypertension, 15(4):339-347 (1990).

Pannier, B. M. et al., "Methods and devices for measuring arterial compliance in humans," American Journal of Hypertension, 15(8):743-753 (2002).

Terry, J. D. et al., "Peak systolic velocity and flow volume increase with blood pressure in low resistance systems," Journal of Ultrasound in Medicine, 14(3):199-203 (1995).

Final Office Action dated Jun. 22, 2022, for U.S. Appl. No. 15/527,467, 12 pages.

\* cited by examiner

PULSE WAVE VELOCITY, ARTERIAL COMPLIANCE, AND BLOOD PRESSURE

CROSS REFERENCE

This application claims the benefit of the filing date of U.S. Provisional Patent Application Ser. No. 62/080,740, filed Nov. 17, 2014, and U.S. Provisional Patent Application Ser. No. 62/080,738, filed Nov. 17, 2014, each of which are hereby incorporated by reference in their entirety.

FIELD

The present disclosure relates to methods for determining blood pressure and arterial compliance of a subject.

BACKGROUND

The pulse wave, generated by left ventricular ejection, propagates at a velocity that has been identified as an important marker of atherosclerosis and cardiovascular risk. Increased pulse wave velocity indicates an increased risk of stroke and coronary heart disease. This velocity is considered a surrogate marker for arterial compliance, is highly reproducible, and is widely used to assess the elastic properties of the individual or series of vessels within the arterial tree. Research shows that measurement of pulse wave velocity as an indirect estimate of aortic compliance could allow for early identification of patients at risk for cardiovascular disease. The ability to identify these patients would lead to better risk stratification and earlier, more cost-effective preventative therapy. Several studies have shown the influence of blood pressure and left ventricular ejection time (LVET) on pulse wave velocity.

Over the past decades, there has been ongoing research for better theoretical relationship between PWV and physiologic parameters. These models typically take the form of a prediction of PWV from parameters such as the geometry and vessel material properties. The clinical use of these is more often to measure PWV and then use the relationships to solve for a physiologic property. To date, the relationships between PWV and arterial stiffness that are used clinically are often based on classic linear models or the combination of the linear models, and measured results with an incorporated correction factor. Whereas linear models predict PWV as a function of only geometric and physical properties of the fluid and the wall, there is strong empirical evidence that PWV is also correlated to pressure and ejection time.

While both pressure and LVET are shown clinically to affect pulse wave velocity, a predictive model that provides mechanistic insight, and incorporates peak pressure, ejection time, ejection volume, and modulus of elasticity has yet to be developed. There are no existing models that enable solution of the inverse problem of determination of aortic compliance parameters and blood pressure from a PWV measure.

The non-invasive and continuous measurement of blood pressure has been attempted using empirically derived models based on the Moens-Korteweg (M-K) speed of propagation. According to linearized acoustics model, the M-K speed of propagation is a constant, dependent on Young's modulus, wall thickness, radius, and blood density. Since the M-K speed is pressure independent, which contradicts to the experimental data, some authors integrate pressure into the acoustics M-K expression assuming that elastic modulus is an exponential function of pressure.

SUMMARY

In accordance with one aspect of the present disclosure there is provided a method for determining a blood pressure of a subject, the method includes providing a value for pulse wave velocity within an arterial segment or segments of a subject; providing a value for flow velocity within the arterial segment or segments of the subject; providing a value for an arterial compliance parameter of the subject; and applying a model of fluid-structure interaction incorporating conservation of mass and momentum for the fluid, and linear elasticity of the structure, to calculate blood pressure of the subject using the provided values.

In accordance with another aspect of the present disclosure there is provided a method for determining an arterial compliance parameter of a subject, the method includes providing a value for pulse wave velocity within an arterial segment or segments of a subject; providing a value for flow velocity within the arterial segment or segments of the subject; providing a value for blood pressure of the subject; and applying a model of fluid-structure interaction incorporating conservation of mass and momentum for the fluid, and linear elasticity of the structure, to calculate an arterial compliance parameter of the subject using the provided values.

In accordance with another aspect of the present disclosure there is provided a method for determining an arterial compliance parameter of a subject under stationary conditions including providing one of an arterial diameter or radius associated with a first pressure; providing one of an arterial diameter or radius associated with a second pressure; and calculating an arterial compliance parameter by finding the difference between the first pressure arterial radius and the second pressure arterial radius, dividing by the difference of the product of the first pressure and the first radius and the product of the second pressure and the second radius, and multiplying by two.

These and other aspects of the present disclosure will become apparent upon a review of the following detailed description and the claims appended thereto.

DETAILED DESCRIPTION

Disclosed are methods for determining physiological parameters of an individual including blood pressure, arterial compliance, flow velocity, and pressure wave velocity. A noninvasive method for determining the blood pressure of a patient based on measurements of flow velocity, pulse wave velocity and arterial compliance is described. Also described is a noninvasive method for determining the arterial compliance of a patient based on measurements of blood pressure, flow velocity, and pulse wave velocity. In an embodiment, the implementation may require some method to measure the pulse wave velocity and this would most likely be a photoplethysmograph, or tonometry or some existing device that measures pulse passing the sensor. Some implementations of the method require a one-time measurement to help calibrate terms within the model and these might include ultrasound imaging to monitor the dynamic behavior of the arterial blood flow, blood pressure measured with a cuff, or a measurement of the vessel size. These measurements, coupled with a mathematical model of the arterial blood flow motion in an elastic vessel constitute a method for determination of either vessel material properties (distensibility) or blood pressure. Derived mathematical models create the patient specific dependence of a blood pressure verses PWV and blood velocity, which allows continuous monitoring of vessel properties (distensibility) or arterial blood pressure. The same model presents an arterial compliance and distensibility as a clinical marker of arterial stiffness. The methodology is particularly applicable for linear elastic vessels (vessels <4 mm outer diameter), for example, that are commonly found in the posterior vessels of the arm, leg, and head.

Figure 1:
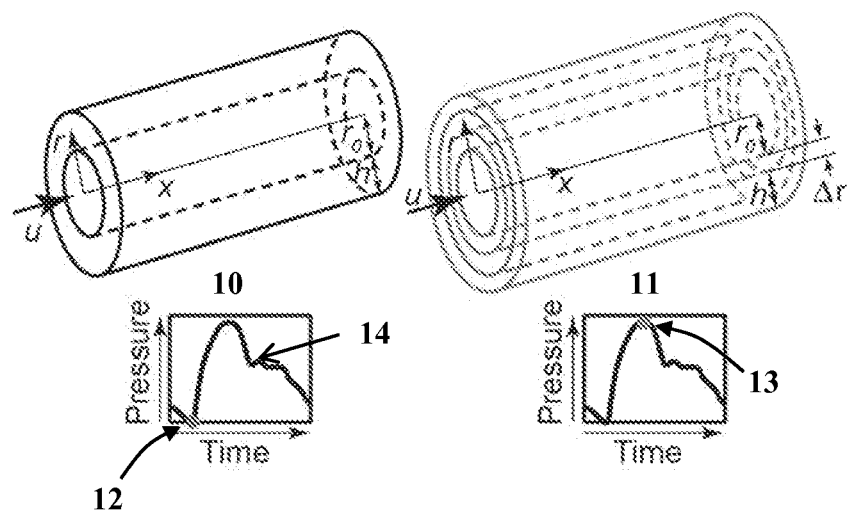
FIG. 1 is a diagram of the longitudinal cross section of the arterial wall at diastolic (10) and systolic (11) pressure.

A mathematical model for pulse wave velocity propagation is disclosed. A nonlinear one-dimensional model for blood pressure wave propagation in compliant arteries was created. This model assumes a compliant tube with a linear elastic wall filled with an incompressible inviscid fluid. As shown in FIG. 1, a longitudinal cross section of the arterial wall being modeled in the r, x plane, where r, x are the radial and axial coordinates, respectively. The cylinder is represented at two specific times in the cardiac cycle, diastolic pressure (item 10) (shown by lowest pressure 12) and systolic pressure (item 11) (shown by peak pressure 13). The wall thickness h, initial inner diameter $r_0$, and wall displacement $\Delta r$ are exaggerated for the purpose of illustration.

At each spatial location x and at each time t the cross sectional axial flow velocity u=u(x,t), static pressure p=p(x,t), cross sectional area A=A(x,t), and membrane circumferential strain (ratio of the normal displacement to the radius) $\eta=\eta(x,t)$ are calculated. Applying the laws of conservation of mass and conservation of momentum results in the following set of 1D equations, correspondingly:

$$A_t + (uA)_x = 0 \tag{1}$$

$$u_t + \left(\frac{u^2}{2} + \frac{p}{\rho}\right)_x = 0 \tag{2}$$

where: $\rho$ is the density of the fluid, assumed to be constant. Subscripts indicate partial derivative by the corresponding space and time variables (x,t), respectively. Equilibrium conditions maintain the relationship between pressure and a circumferential stress:

$$p = \frac{\bar{E}h}{r_0}\eta \tag{3}$$

where: E is the elastic modulus for the wall, $\nu$ is Poisson coefficient; and $\bar{E}=E/(1-\nu^2)$; h is the constant thickness of the wall, $r_0$ is the cross sectional radius of the unstressed cylindrical vessel (p=0), and $\eta$ is circumferential wall strain.

Noting that $A=\pi r_0^2 (1+\eta)^2$, the total system of equations can be presented in the following non-conservative form:

$$\eta_t + u\eta_x + \frac{1+\eta}{2}u_x = 0 \tag{4}$$

$$u_t + uu_x + \frac{1}{\rho}p_x = 0 \tag{5}$$

$$p = \frac{\bar{E}h}{r_0}\eta \tag{6}$$

We are looking for the solitary traveling wave solution in a form $\eta(x,t)=\eta(X)$, $u(x,t)=u(X)$, where $X=x-ct$ and c represents the velocity of the traveling wave. The functions $\eta(X)$, $u(X)$, $p(X)$ are assumed to be smooth, and decaying monotonically as $X\to\pm\infty$.

Substituting $\eta(X)$, $u(X)$ into equations (4-6), we obtain the following system of ordinary differential equations where prime indicates the derivative with respect to X:

$$(-c+u)\eta' + \frac{1}{2}(\eta+1)u' = 0 \tag{7}$$

$$-cu' + uu' + \frac{\bar{E}h}{\rho r_0}\eta' = 0 \tag{8}$$

A non-trivial solution exists only if $$\left\| \begin{matrix} -c+u & \frac{1}{2}(\eta+1) \\ \frac{\bar{E}h}{\rho r_0} & -c+u \end{matrix} \right\| = 0,$$

wherefrom $$c = u \pm \sqrt{\frac{\bar{E}h(\eta+1)}{2r_0\rho}} \tag{9}$$

Associating pulse wave velocity (PWV) with the forward running wave arrive to the following explicit expression $$PWV = u + c_{MK}\sqrt{1 + \frac{pr_0}{\bar{E}h}} \tag{10}$$

where $$c_{MK} = \sqrt{\frac{\bar{E}h}{2r_0\rho}} \tag{11}$$

is the Moens-Korteweg speed of propagation which is a function of the mechanical properties of the system only. Equation (10) describes corrections to the classical Moens-Korteweg model, dependent on pressure and a flow velocity. According to the classical M-K traveling wave model, pressure, flow, and wall displacement propagate with the same speed of propagation c (or PWV), referred to here as the Moens-Korteweg speed ($c_{MK}$). According to the proposed model derived here and presented in equation (10), model and, accounting for nonlinearities predicts a speed of propagation that exceeds $c_{MK}$. As expected for soliton nonlinear waves, the higher peak pressure wave travels with a higher speed. As ejection time decreases, the flow velocity u increases, thereby increasing PWV as seen in equation (10).

As it follows from equation (10), blood pressure prediction uses measurements of PWV and a measurement or an estimate of flow velocity u, and can be calculated as $$p = 2/D * [(PWV_f/c_{MK})^2 - 1] \quad (12)$$

In which $PWV_f = (PWV - u)$ is the pulse wave velocity with respect to the flow velocity; $D = 2\, r_0/Eh$ represents the distensibility.

Assessment of arterial compliance and distensibility is disclosed. Arterial stiffness, or its related parameters, arterial compliance and distensibility, may provide indication of vascular changes that predispose to the development of major vascular disease. In an isolated arterial segment filled with a moving fluid, compliance is defined as a change of a volume $\Delta V$ for a given change of a pressure $\Delta p$, and distensibility as a compliance divided by initial volume. According to definition the local compliance C and distensibility D are $$C = \frac{dV}{dp}, D = \frac{c}{V} = \frac{dV}{Vdp} \quad (13)$$

which with the help of (6), (11) results in relations between distensibility and the Moens-Kortweg speed of propagation $$D = \frac{2r_0}{Eh} = \frac{1}{\rho c_{MK}^2}, C = VD \quad (14)$$

Unlike empirical approaches the present physics based model identifies rigorously the set of independent variables affecting PWV. Substituting (14) into (10) the PWV can be presented as a function of three independent variables: pressure, flow velocity and distensibility $$PWV = u + \sqrt{\frac{1}{\rho D}\left(1 + \frac{pD}{2}\right)} \quad (15)$$

Equation (15) can be easily inverted to identify distensibility based on measured PWV, flow velocity and pressure $$D = \left[\rho * PWV_f^2 - \frac{p}{2}\right]^{-1} \quad (16)$$

Rewriting equation (16) to solve for pressure results in $$p = \frac{2(\rho D(PWV - u)^2 - 1)}{D} \quad (17)$$

A calibration Method for a PWV-based blood pressure measurement is disclosed. Determination of blood pressure with equation (17) requires calibration for arterial distensibility either directly on the subject or using data representative of a specific population demographic.

A PWV based method for determining an arterial compliance is disclosed. Assume we have a set of measurements for PWV, flow velocities and pressures: $PWV_i$, $u_i$, $p_i$, i=1, ..., N. An average arterial distensibility is determined based on the N measures and equation (16) as shown in equation (18)

$$D = \left[\frac{\sum_{i=1}^{N}\left(\rho * PWV_f^2 - \frac{p}{2}\right)_i}{N}\right]^{-1} \quad (18)$$

The blood density $\rho$ can be estimated based on historic data, or measured with a blood draw and established fluid density measures. Here the pressure p can be systolic, diastolic, or any intermediate pressure (e.g. mean pressure) when coupled with the appropriate flow velocity (u). For example, systolic pressure could be associated with the peak flow velocity, and diastolic pressure could be associated with the lowest (or zero) flow velocity. Or an average pressure could be associated with an average flow velocity. The PWV measure can be made to associate with diastolic pressure (e.g. foot of the pressure waveform, FIG. 1—item 12), systolic pressure (peak of the pressure waveform, FIG. 1—item 13), or any intermediate pressure (e.g. mean pressure).

An ultrasound based measurement for determining an arterial distensibility or compliance is disclosed. An in vivo pressure measurements and ultrasound based estimation of a systolic with respect to diastolic wall displacement allows to detect a linear elastic Young's modulus. Applying Laplace's law to systolic and diastolic phases of a cardiac cycles arrive to the following equations $$\frac{p_s r_s}{h} = E\frac{W_s}{r_0} \quad (19)$$

$$\frac{p_d r_d}{h} = E\frac{W_d}{r_0}$$

The following notations are introduced: indices s and d—indicate systolic and diastolic parameters respectfully, p—transmural pressure, r—radius of the artery, h—wall thickness of the artery, W—normal displacement of the artery with respect to the load free state. The relative displacement $W_s - W_d$ can be measured directly as a difference of relating radii. By subtracting the second equation from the first one, and introducing distensibility parameter from (14), obtain an expression for the arterial distensibility (20).

$$D = 2\frac{r_s - r_d}{p_s r_s - p_d r_d} \quad (20)$$

Figure 4:
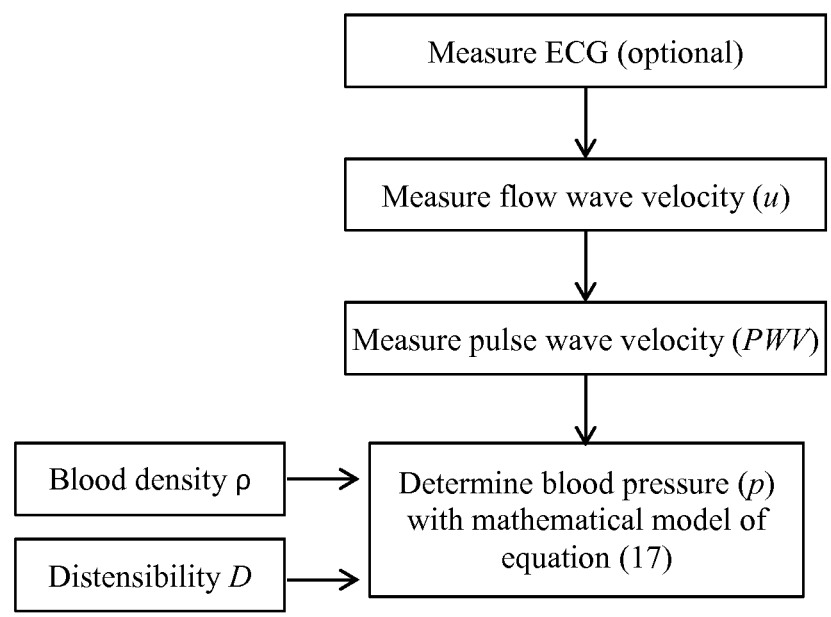
FIG. 4 is a flowchart of a method for determining blood pressure of a subject based on a PWV measure.

A method for determining the blood pressure of a subject is disclosed. An embodiment of a method for determining a subject's blood pressure is shown in FIG. 4. An ECG measurement can be made for use as a timing reference for start of the pulse wave transit time, or to be used as a reference for determining acceptance time windows for other waveform features, or for averaging waveforms. An arterial flow velocity is measured providing minimum and maximum flow velocities, although a minimum could be assumed to be zero. An average flow velocity can also be measured. The flow velocity can also be estimated based on other measures or as a percentage of PWV. The pulse wave velocity is measured, ideally providing both a systolic and diastolic PWV. The subject (or population based) distensibility parameter (D), and subject (or population based) blood density ρ are then used with the mathematical model of equation 17 to estimate blood pressure. The systolic PWV and the peak flow velocity are used to estimate a systolic blood pressure, while a diastolic PWV and the minimum flow velocity are used to estimate a diastolic blood pressure. Although other estimates and combinations may be used to estimate an average or systolic or diastolic blood pressure.

An optional ECG can be measured across the chest and wrists. Other locations are also possible such as ear lobes, behind the ears, buttocks, thighs, fingers, or feet/toes. PPG can be measured at the chest and wrist. Other locations such as the ear lobes, fingers, forehead, buttocks, thighs, and toes also work. Video analysis methods examining changes in skin color can also be used to obtain a PPG waveform. Flow velocity can be measured at the chest or wrist. Other locations for flow velocity measure are also possible (neck, arm, leg, and the like).

In one embodiment, the pulse transit time is measured based on aortic valve opening determined by the J-wave of the BCG waveform, and a PPG foot measured (e.g., FIG. 1, item 12) from the thigh. The ECG r-wave may be used as a reference for determining acceptance windows for BCG and PPG feature delineations, or as a starting point for a PWV measure. The aorta distance is estimated from aortic root along the path of the aorta to the femoral artery at the thigh PPG measurement location. The PWV is calculated by dividing the aorta distance by the measured time difference (BCG J-wave to PPG foot). The minimum and maximum flow velocity is measured by ultrasound Doppler at the aortic root. A blood density ρ is assumed based on age and gender of the subject. Using the calibrated arterial compliance parameter distensibility (D) for the subject, the pressure will be calculated based on the referenced equation (17) or using a pre-calculated lookup table. To calculate $p_d$ the minimum measured flow velocity can be used in combination with an estimate of diastolic PWV. To calculate $p_s$ the peak flow velocity or a percentage of the peak flow velocity can be used in combination with an estimate of systolic PWV. Under conditions where flow velocity is not measured, diastolic flow velocity can be assumed to be 0, while systolic flow velocity can be estimated as a percentage of PWV (e.g ~20%). In cases where a systolic PWV cannot be measured directly, the systolic flow velocity (u) can be added to a PWV measured at the foot as an estimate of systolic $PWV_f$.

In another embodiment, the pulse transit time is measured from the carotid artery using tonometry, to the pressure pulse measured at thigh with a thigh cuff. The arterial distance is estimated from aortic root along the path of the aorta to the femoral artery at the thigh cuff measurement location. The PWV is calculated by dividing the arterial distance by the measured time difference. The foot to foot timing on the measured pressure pulses (e.g., FIG. 6, items 801 and 810) is used to determine a diastolic pulse transit time and to calculate a diastolic PWV. The peak to peak timing (e.g., FIG. 6, items 802 and 811) is used to determine a systolic pulse transit time and to calculate a systolic PWV. The peak flow velocity is estimated at 20% of the systolic PWV while the minimum flow velocity is estimated at zero. A blood density ρ is assumed based on age and gender of the subject. Using the calibrated arterial compliance parameter distensibility (D) for the subject, the pressure will be calculated based on the referenced equation (17)) or using a pre-calculated lookup table. To calculate $p_d$ the minimum measured flow velocity can be used in combination with the diastolic PWV. To calculate $p_s$ the peak flow velocity is used in combination with the systolic PWV.

Figure 2:
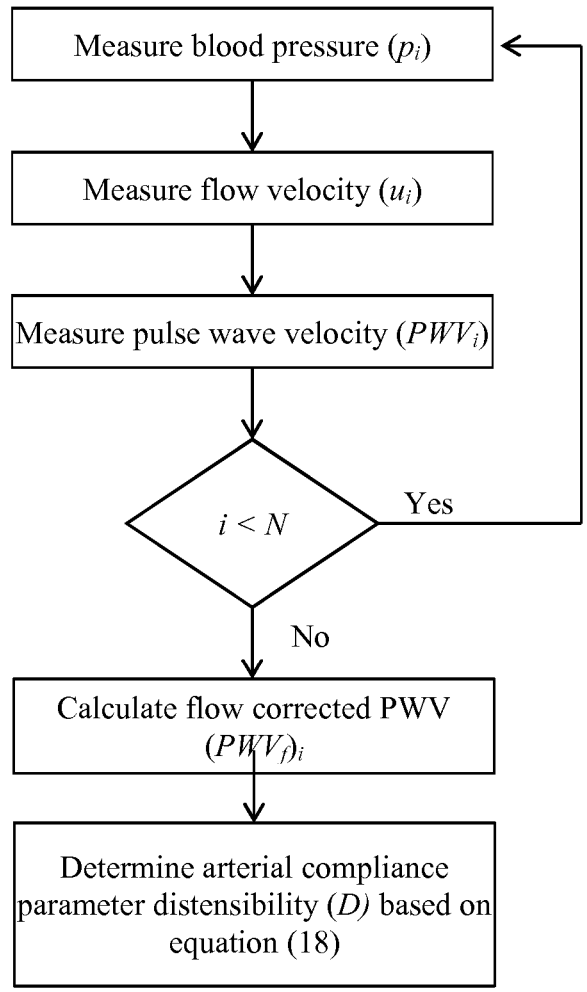
FIG. 2 is a flowchart of a PWV based method to determine a subject arterial compliance parameter.

A method for determining an arterial compliance parameter of a subject is disclosed. In an embodiment a flow chart for a PWV based method for determining an arterial compliance parameter for a subject is shown in FIG. 2. The three input arrays of N depth (including N=1) are created: blood pressure, flow velocity, and PWV. Arrays of i measures can be created with multiple measurements within a single cardiac cycle, or by modulation of physiological state. Physiological state can be changed through pharmaceuticals, position (e.g., standing, sitting, prone, and inverted), exercise, isometric exercise, or the Valsalva maneuver. Ideally these measures would be time synchronized and simultaneously captured, although serial, sequential measurements can also be used.

Figure 6:
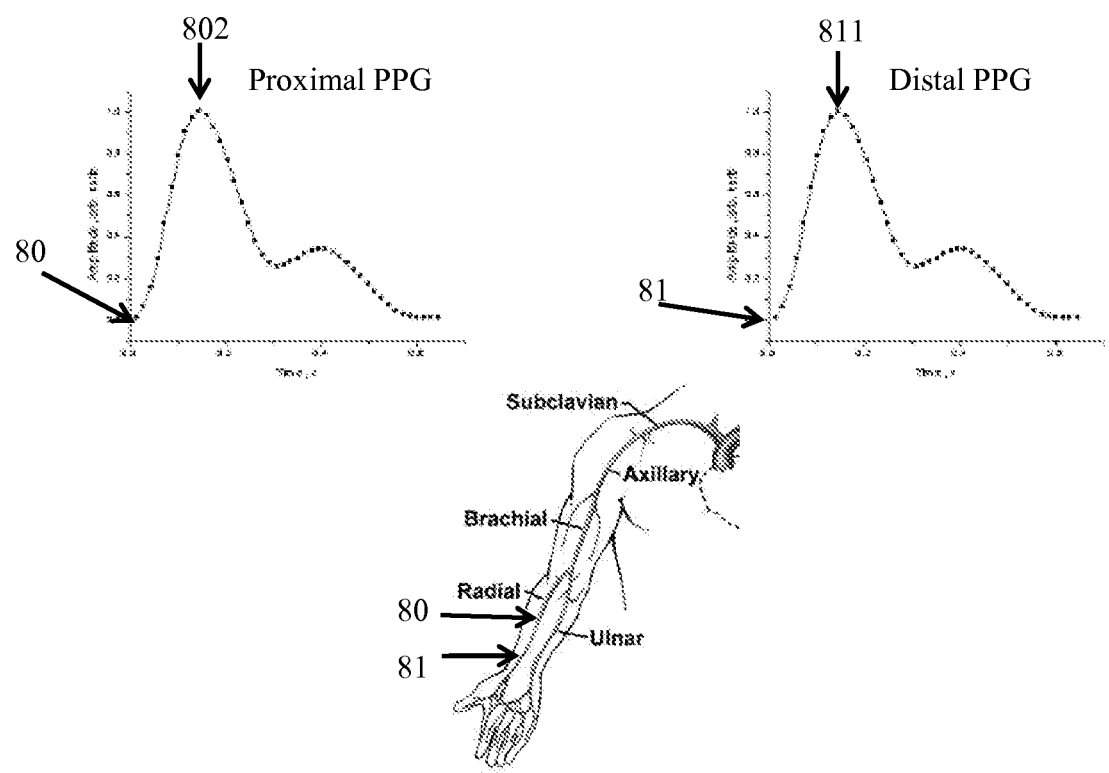
FIG. 6 is an illustration of pressure pulse measurement on two locations in the same artery for determination of a systolic and diastolic PWV.

Determination of PWV requires measurement of the transit time of the pulse wave between two points, and a measure or estimate of the distance traveled. The PWV is the distance travelled divided by the time difference. This can be done by extracting the foot (FIG. 1, item 12) or peak (FIG. 1, item 13) of the pressure wave in two locations (proximal, distal) of the same artery, calculating the time difference between these two extracted features, and measuring the distance between these two measurement points. In one embodiment, this is done in the radial artery as shown in FIG. 6 with measurements items 80 (proximal) and 81 (distal). Use of the foot location on the pressure or PPG waveform (items 801 and 810) will correlate to a diastolic PWV, while use of the peak location (items 802 and 811) will correlate to a systolic PWV. Two different arteries can also be used with a measurement or estimate of the arterial path distance between the two measurement points. The PWV can also be measured using the heart as the proximal measurement point with an electrocardiogram feature (e.g., the ECG r-wave) as the first time point, or by sensing when the aortic valve opens using a feature on measured waveforms or images such as the ballistocardiogram (BCG), ultrasound imaging, Doppler ultrasound, impedance plethysmography (IPG), or photoplethysmography (PPG) on the chest over the aorta. The distal pressure wave is then used as above to extract a second time point. The arterial distance between the aortic root and the distal measurement point is used in the calculation of PWV. This can be measured or estimated, and may be based on subject characteristics such as height, weight age and gender. The distal pressure wave can be measured using sensors such as tonometry, an arterial cuff, ultrasound, RF based arterial wall tracking, and PPG.

Measurement of flow velocity can be done using Doppler ultrasound, an inductive coil, MRI or CT scan with contrast agents. The flow velocity can be captured as a continuous wave, as a peak value, or a minimum value (including u=0). It is also possible to estimate flow velocity using related measures or with a scale factor. For example PWV can be measured using previously described techniques and flow velocity is then estimated as a percentage of PWV (for example u=0.2 PWV). Aortic flow velocity can be estimated through left ventricular ejection time (LVET), ejection volume (EV), and aortic cross-sectional area (CA) where u=EV/(LVET*CA). Left ventricular ejection time (LVET) can be measured or estimated using a number of sensors (e.g. PPG, heart sound). Using PPG for example, the measure of LVET is the length of time from the foot of the PPG wave (FIG. 1 item 12) to the dicrotic notch (item 14). Using heart sound, LVET is the time between the first and second heart sound. Ejection volume can be based on direct measurement for the subject (e.g. ultrasound, thermal dilution, etc) at rest and at exercise with subsequent scaling based on heart rate. The cross-sectional area can be directly measured by ultrasound imaging, MRI, or CT scans. EV and CA can also be based on subject specific parameters such as age, gender, height and weight. EV can also be measured or estimated using features from the BCG such as the amplitude of the j-wave or m-wave. An estimate of flow velocity in the periphery can be made based on scaling of the blood volume in that arterial tree branch, and relative arterial size as compared to the aorta. Although a direct measurement of flow velocity or an estimate based on PWV is preferred in the periphery.

Pressure can be measured using any approved technique, for example, brachial cuff, tonometry, or intra-arterial catheter. Ideally a continuous method (e.g. tonometry, intra-arterial) is used with a method of time synchronization to the flow and PWV measures (e.g. via ECG). However serial measures can also be used. Here the pressure p can be systolic, diastolic, or any intermediate pressure (e.g., mean pressure) when coupled with the appropriate flow velocity (u). For example, systolic pressure could be associated with the peak flow velocity, and diastolic pressure could be associated with the lowest (or zero) flow velocity, or an average pressure could be associated with an average flow velocity.

Once the blood pressure, flow velocity, and PWV have been measured, a flow corrected PWV ($PWV_f$) may be calculated as described below in equation (12). This can use the measured flow velocity, an estimate, or may be set to zero.

The blood density $\rho$ can be estimated based on historic data, or measured with a blood draw and established fluid density measures.

The distensibility (D) is calculated based on the mathematical model of equation (18). Population based estimates of any of these parameters may be used in combination with measured values to provide an estimate of D. These population estimates can be based on age, gender, and medical history, by way of example only.

In some embodiments, the wave will propagate across multiple arterial segments between the proximal and distal points of pressure measurement. This measurement can be used in at least two ways. In the first form, average properties of the vessel segments, radius, and modulus will be considered so that the result corresponds to bulk average of the segment. In the second, the properties of individual arterial segments are determined. First, use the model to determine the relative transit time through each sequential arterial segment based on geometrical properties of each segment and assuming a similar pressure within all segments. Then using a solution method, such as minimization of a least squares or another method, solve for the PWV within each segment by recognizing that the total transit time (measured) is the sum of the transit time through each segment.

Figure 3:
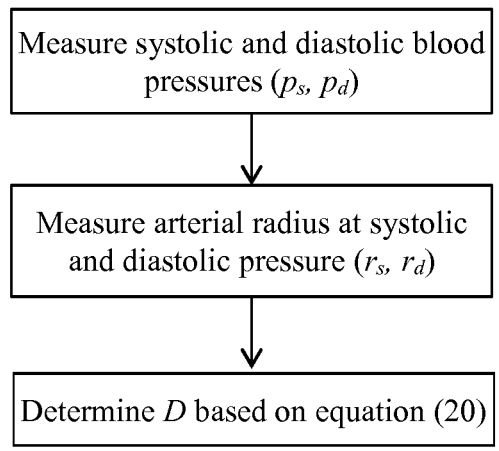
FIG. 3 is a flowchart of a method to determine a subject arterial compliance parameter under stationary conditions.

A method for determining an arterial compliance parameter under stationary conditions is disclosed. For subjects that for various reasons cannot actively change their physiological state (e.g., hospitalized) it is important to have a stationary calibration method. A flow chart for a method to determine a subject arterial compliance parameter under stationary conditions is shown in FIG. 3. Systolic blood pressure ($p_s$) and diastolic blood pressure ($p_d$) are measured along with a measurement of the arterial radius at systolic ($r_s$) and diastolic ($r_d$) pressures.

Pressure can be measured using any approved technique, for example, brachial cuff, tonometry, or intra-arterial catheter. Ideally a continuous method (e.g., tonometry, intra-arterial) is used with a method of time synchronization to the other measurements (e.g., via ECG). However, the minimum and maximum radii can be assumed to correlate to the diastolic and systolic blood pressures respectively, enabling a non-continuous measure (e.g., cuff-based) to be utilized.

The arterial radius at diastolic and systolic pressures is measured using a technique such as ultrasound imaging to identify the wall position throughout the cardiac cycle. Other approaches such as MRI or CT coupled with a contrast agent may also be used. Wall thickness can be measured using these same approaches.

An arterial compliance parameter, distensibility, may then be calculated using equation (20).

Population based estimates of any of these parameters may be used in combination with measured values to provide an estimate of D. These population estimates can be based on age, gender, and medical history, by way of example only.

Figure 5:
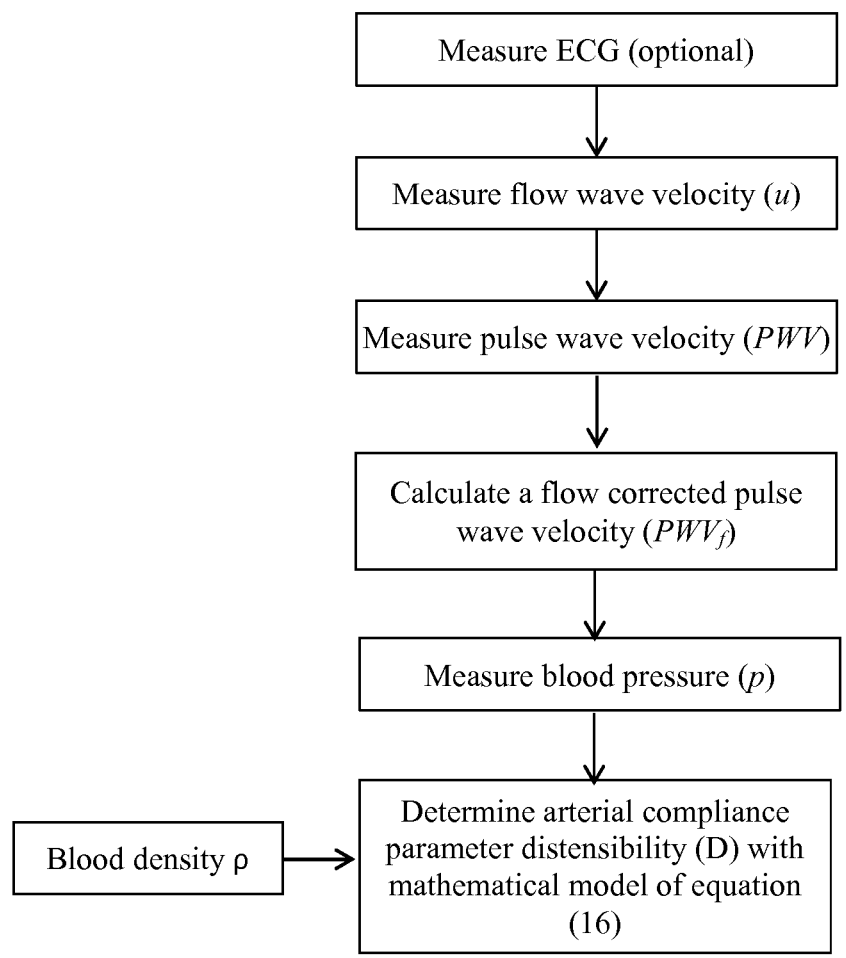
FIG. 5 is a flowchart of a method for determining the arterial compliance parameter of a subject based on a PWV and blood pressure measure.

An embodiment of a method for monitoring a subject's arterial compliance is shown in FIG. 5. An ECG measurement can be made for use as a timing reference for start of the pulse wave transit time, or to be used as a reference for determining acceptance time windows for other waveform features, or for averaging waveforms. An arterial flow velocity is measured providing minimum and maximum flow velocities, although a minimum could be assumed to be zero. An average flow velocity can also be measured. The flow velocity can also be estimated based on other measures or as a percentage of PWV. The pulse wave velocity is measured, ideally providing both a systolic and diastolic PWV. The blood pressure is measured using a brachial cuff or other established method, providing systolic, diastolic, or mean pressure. The subject (or population based) blood density $\rho$ is then used with the mathematical model of equation (16) to estimate the subject arterial compliance factor distensibility (D).

The systolic PWV and the peak flow velocity are used in combination with a systolic blood pressure, while a diastolic PWV and the minimum flow velocity are used with a diastolic blood pressure. Although other estimates and combinations may be used to determine the subject distensibility parameter.

An optional ECG can be measured across the chest and wrists. Other locations are also possible such as ear lobes, behind the ears, buttocks, thighs, fingers, or feet/toes. PPG can be measured at the chest and wrist. Other locations such as the ear lobes, fingers, forehead, buttocks, thighs, and toes also work. Video analysis methods examining changes in skin color can also be used to obtain a PPG waveform. Flow velocity can be measured at the chest or wrist. Other locations for flow velocity measure are also possible (neck, arm, leg, and the like).

In one embodiment, the pulse transit time is measured based on aortic valve opening determined by the J-wave of the BCG waveform, and a PPG foot measured (e.g., FIG. 1, item 12) from the thigh. The aorta distance is estimated from aortic root to femoral artery at the thigh PPG measurement location. The PWV is calculated by dividing the aorta distance by the measured time difference (BCG J-wave to PPG foot). The minimum flow velocity is assumed to be zero, enabling distensibility calculation without a direct flow measurement. The flow corrected PWV is calculated (in this embodiment $PWV_f$=PWV since u=0). A blood density $\rho$ is assumed based on age and gender of the subject. Blood pressure is taken using the cuff on the brachial artery. The diastolic blood pressure is used in combination with equation 16 and $PWV_f$, ρ, and the diastolic blood pressure to calculate an aortic distensibility (D) for the subject. The calculated D may be used in combination with equation (14) and measures of aortic diastolic radius ($r_0$) and wall thickness (h) (e.g., based on prior ultrasound measures) to calculate a Young's modulus (E). Measures of a systolic PWV, peak flow velocity, and systolic pressure may also be used to determine D.

In another embodiment, the pulse transit time is measured from the carotid artery using tonometry, to the pressure pulse measured at thigh with a thigh cuff. The arterial distance is estimated from aortic root along the path of the aorta to the femoral artery at the thigh cuff measurement location. The PWV is calculated by dividing the arterial distance by the measured time difference. The foot to foot timing on the measured pressure pulses (e.g., FIG. 6 items 801 and 810) is used to determine a diastolic pulse transit time and to calculate a diastolic PWV. The peak to peak timing (e.g., FIG. 6, items 802 and 811) is used to determine a systolic pulse transit time and to calculate a systolic PWV. The peak flow velocity is estimated at 20% of the systolic PWV while the minimum flow velocity is estimated at zero. A blood density ρ is assumed based on age and gender of the subject. The systolic and diastolic blood pressure for the subject is measured on the brachial artery using a pressure cuff. This pressure may be translated to an aortic pressure, or may be used directly. The arterial compliance parameter distensibility (D) is then calculated using the mathematical model of equation (16). The systolic blood pressure can be used with the peak flow velocity and the systolic PWV to determine D. Alternatively, the diastolic blood pressure can be used with the minimum flow velocity and diastolic PWV to determine D. Either of these estimates of D may be used, or the results may be averaged to provide an average D.

An embodiment includes a method for determining an arterial compliance parameter of a subject includes providing a value for pulse wave velocity within an arterial segment or segments of a subject; providing a value for flow velocity within the arterial segment or segments of the subject; providing a value for blood pressure of the subject; and applying a model of fluid-structure interaction incorporating conservation of mass and momentum for the fluid, and linear elasticity of the structure, to calculate an arterial compliance parameter of the subject using the provided values. The method further includes wherein the pulse wave velocity and flow are provided at different blood pressures. The method further includes wherein the blood pressure is provided as a continuous blood pressure waveform. The method further includes wherein the blood pressure is measured using tonometry. The method further includes wherein the blood pressure is measured using a cuff providing at least one of a systolic, diastolic, or mean blood pressure. The method further includes wherein blood pressure is measured with an intra-arterial catheter to provide a continuous blood pressure waveform. The method further includes wherein the flow wave velocity is subtracted from the pulse wave velocity to provide a flow corrected pulse wave velocity. The method further includes wherein the flow wave velocity is estimated as a percentage of the pulse wave velocity. The method further includes wherein the peak pulse wave velocity is associated with a systolic pressure. The method further includes wherein the minimum pulse wave velocity is associated with a diastolic pressure. The method further includes wherein the peak flow velocity is associated with a systolic pulse wave velocity. The method further includes wherein the minimum flow velocity is associated with a diastolic pulse wave velocity. The method further includes wherein physiologic state of the subject is varied by exercise to allow a range of at least one of blood pressure, pulse wave velocity, and flow velocity to be measured. The method further includes wherein physiologic state of the subject is varied by isometric exercise to allow a range of at least one of blood pressure, pulse wave velocity, and flow velocity to be measured. The method further includes wherein physiologic state of the subject is varied by pharmaceuticals to allow a range of at least one of blood pressure, pulse wave velocity, and flow velocity to be measured. The method further includes wherein physiologic state of the subject is varied by the Valsalva maneuver to allow a range of at least one of blood pressure, pulse wave velocity, and flow velocity to be measured. The method further includes wherein the arterial compliance parameter is a distensibility. The method further includes wherein the arterial compliance parameter is a Young's modulus. The method further includes wherein the arterial compliance parameter is a compliance.

An embodiment includes a method for determining an arterial compliance parameter of a subject under stationary conditions including providing one of an arterial diameter or radius associated with a first pressure; providing one of an arterial diameter or radius associated with a second pressure; calculating an arterial compliance parameter by finding the difference between the first pressure arterial radius and the second pressure arterial radius, dividing by the difference of the product of the first pressure and the first radius and the product of the second pressure and the second radius, and multiplying by two.

An embodiment includes a method for determining a blood pressure of a subject including providing a value for pulse wave velocity within an arterial segment or segments of a subject; providing a value for flow velocity within the arterial segment or segments of the subject; providing a value for an arterial compliance parameter of the subject; and applying a model of fluid-structure interaction incorporating conservation of mass and momentum for the fluid, and linear elasticity of the structure, to calculate blood pressure of the subject using the provided values. The method further includes wherein the pulse wave velocity is measured. The method further includes wherein the pulse wave velocity is estimated based on measures of flow velocity. The method further includes wherein the flow velocity is measured. The method further includes wherein the flow velocity is estimated based on a percentage of pulse wave velocity. The method further includes wherein flow velocity is estimated based on ejection volume, aortic cross-sectional area, and left ventricular ejection time. The method further includes wherein arterial compliance parameters are based at least one of age, gender, disease history, height, or weight. The method further includes wherein arterial compliance parameter is a distensibility. The method further includes wherein arterial compliance parameter is a Young's modulus. The method further includes wherein the arterial compliance parameter is a compliance. The method further includes wherein the arterial compliance parameter is determined based on a subject calibration. The method further includes wherein the arterial compliance parameter is based on population statistics. The method further includes wherein the model is embodied as a lookup table. The method further includes wherein the peak pulse wave velocity is associated with a systolic pressure. The method further includes wherein the minimum pulse wave velocity is associated with a diastolic pressure. The method further includes wherein the peak flow velocity is associated with a systolic blood pressure. The method further includes wherein the minimum flow velocity is associated with a diastolic blood pressure.

An embodiment includes a method for measuring the pulse wave velocity of a subject including measuring a first signal associated with the pulse wave; measuring a second signal associated with the pulse wave at a location physically removed from the first; providing a distance between the first and second measurement point; subtracting the time of the first signal from the time of the second signal; and dividing distance by the time difference. The method further includes wherein the pulse wave velocity is measured between two points on the same artery. The method further includes wherein the pulse wave velocity is measured foot to foot to provide a minimum pulse wave velocity. The method further includes wherein the pulse wave velocity is measured peak to peak to provide a peak pulse wave velocity. The method further includes wherein the pulse wave velocity first timing point is based on the electrocardiogram r-wave and the second timing point is measured at the periphery. The method further includes wherein the pulse wave velocity is measured using a photoplethysmogram over an artery at two points. The method further includes wherein the pulse wave velocity is measured using impedance at two points. The method further includes wherein the pulse wave velocity first timing point is based on a chest impedance measurement and the second timing point is measured at the periphery.

An embodiment includes a method for measuring the flow velocity of a subject including providing a sensor over an arterial segment; measuring a signature related to blood flow; and calculating a flow velocity. The method further includes wherein the sensor is Doppler ultrasound. The method further includes wherein the sensor is an inductive coil. The method further includes wherein the sensor measures chest impedance. The method further includes wherein a combination of sensor measurements are used including left ventricular ejection time, ejection volume, and aortic cross-sectional area. The method further includes wherein the flow velocity is estimated as a percentage of the pulse wave velocity.

The disclosure will be further illustrated with reference to the following specific examples. It is understood that these examples are given by way of illustration and are not meant to limit the disclosure or the claims to follow.

EXAMPLES

Paper Example 1, Blood Pressure

This paper example uses referenced values for a female 20-30 years of age to simulate blood pressure determination. Two PPG sensors are placed on a subject's radial artery, for example 0.23 m apart (FIG. 6, item 81, 82). The PPG waveform is measured from the two sensors and the foot to foot time difference is measured (801,810) for example 46 ms. The diastolic PWV is then calculated as 0.23 m/46 ms=5 m/s. From the same PPG waveform the peak to peak time difference is measured (802,811) for a simulated value of 32.2 ms. The systolic PWV is then calculated as 0.23 m/32.2 ms===7.14 nm/s. Flow velocity is then estimated to be 0 for $p_d$ calculation and 20% of systolic PWV for $p_s$ calculation ($u_d$=0, $u_s$=8.54 m/s×0.2=1.424 m/s. The population based distensibility parameter (D=5×10$^{-5}$ Pa$^{-1}$), and subject (or population based blood density ρ (1060 kg/m$^3$) are referenced and used with the mathematical model of equation 17 to predict blood pressure. This results in a prediction of $p_d$=79 mmHg and a $p_s$=110 mmHg.

Paper Example 2, Distensibility

This paper example uses referenced values for a female 20-30 years of age to simulate distensibility determination. Referencing equation 18, for this example N is set to 2. The subject is allowed to rest for ~20 minutes in a chair before the start of the measurements. Two PPG sensors are placed on a subject's radial artery, for example 0.23 nm apart (FIG. 8, item 81, 82). The PPG waveform is measured from the two sensors and the foot to foot time difference is measured (801,810) for example, 46 ms. The diastolic PWV is then calculated as 0.23 m/46 ms=5 m/s. From the same PPG waveform the peak to peak time difference is measured (802,811) for example, 32.2 ms. The systolic PWV is then calculated as 0.23 m/32.2 ms=7.14 m/s. Flow velocity (min, max) is then measured using Doppler ultrasound at location (FIG. 6, item 80). ($u_d$=0.11, $u_s$=1.23 m/s). The population based blood density ρ (1060 kg/m$^3$) are referenced. Using a blood pressure cuff $p_s$ and $p_d$ are measured on the arm ((122 mmHg, 74 mmHg) or (16265 Pa, 9866 Pa), respectively). Using the mathematical model of equation 18 distensibility is calculated as:

$$\frac{1}{D} = \frac{\left(\rho \times \text{diastolic\_PWV}_f^2 - \frac{p_d}{2}\right) + \left(\rho \times \text{systolic\_PWV}_f^2 - \frac{p_s}{2}\right)}{N}$$

$$\frac{1}{D} = \frac{\left(1060(5.00 - 0.11)^2 - \frac{9866}{2}\right) + \left(1060(7.14 - 1.23)^2 - \frac{16265}{2}\right)}{2}$$

$$D = 40.6 \frac{1}{\text{MPa}} \text{ or } 5.4 \times 10^{-3} \frac{1}{\text{mmHg}}$$

Although various embodiments have been depicted and described in detail herein, it will be apparent to those skilled in the relevant art that various modifications, additions, substitutions, and the like can be made without departing from the spirit of the disclosure and these are therefore considered to be within the scope of the disclosure as defined in the claims which follow.

What is claimed:

1. A method for determining a blood pressure of a subject, the method comprising:

measuring a transit time of a pulse wave between two points of an arterial segment or segments of the subject by capturing one or more waveforms or images using one or more sensors or imaging;

determining a value for pulse wave velocity within the arterial segment or segments of the subject based on the transit time and an arterial distance between the two points;

determining a value for flow velocity within the arterial segment or segments of the subject;

determining a value for an arterial compliance parameter of the subject; and generating a value for the blood pressure p of the subject by applying a model of fluid-structure interaction incorporating conservation of mass and momentum for a fluid, and linear elasticity of a structure, the model of fluid-structure interaction comprising the equation $$p = \frac{2(\rho D(PWV - u)^2 - 1)}{D},$$

where PWV is the pulse wave velocity, u is the flow velocity, $\rho$ is the density of the fluid, and D is the arterial compliance parameter.

2. The method of claim 1, wherein the arterial compliance parameter comprises distensibility.

3. The method of claim 1, wherein the blood pressure is a systolic pressure and the pulse wave velocity is a peak pulse wave velocity.

4. The method of claim 1, wherein the blood pressure is a diastolic pressure and the pulse wave velocity is a minimum pulse wave velocity.

5. The method of claim 1, wherein the blood pressure is a systolic blood pressure and the flow velocity is a peak flow velocity.

6. The method of claim 1, wherein the blood pressure is a diastolic blood pressure and the flow velocity is a minimum flow velocity.

7. The method of claim 1, wherein determining the value for flow velocity includes at least one of: measuring the flow velocity using a sensor, or estimating the flow velocity based on scaling a physiological parameter associated with the flow velocity.

8. The method of claim 1, wherein determining the value for the arterial compliance parameter includes at least one of: measuring the arterial compliance parameter using at least one of a sensor or imaging, or estimating the arterial compliance parameter based on a calculation or a population based estimate.

9. A method for determining an arterial compliance parameter of a subject, the method comprising:
measuring a transit time of a pulse wave between two points of an arterial segment or segments of the subject by capturing one or more waveforms or images using one or more sensors or imaging;
determining a value for pulse wave velocity within the arterial segment or segments of the subject based on the transit time and an arterial distance between the two points;
measuring a value for flow velocity within the arterial segment or segments of the subject;
determining a flow corrected value for the pulse wave velocity based on the value for the flow velocity;
measuring a value for blood pressure of the subject;
receiving a value for blood density of the subject; and
determining the arterial compliance parameter of the subject by applying a model of fluid-structure interaction incorporating conservation of mass and momentum for a fluid, and linear elasticity of a structure, the model of fluid-structure interaction comprising:
populating any one of equations $$D = \left[\rho * PWV_f^2 - \frac{p}{2}\right]^{-1} \text{ or } D = \left[\frac{\sum_{i=1}^{N}\left(\rho * PWV_f^2 - \frac{p}{2}\right)_i}{N}\right]^{-1},$$

where $PWV_f$ is the flow corrected value for the pulse wave velocity, $\rho$ is the density of the fluid, p is the blood pressure, and N is the number of vessels within the arterial segment or segments.

10. The method of claim 9, wherein the arterial compliance parameter comprises distensibility.

11. The method of claim 9, wherein the blood pressure is a systolic pressure and the pulse wave velocity is a peak pulse wave velocity.

12. The method of claim 9, wherein the blood pressure is a diastolic pressure and the pulse wave velocity is a minimum pulse wave velocity.

13. The method of claim 9, wherein the blood pressure is a systolic blood pressure and the flow velocity is a peak flow velocity.

14. The method of claim 9, wherein the blood pressure is a diastolic blood pressure and the flow velocity is a minimum flow velocity.

15. The method of claim 9, wherein determining the flow corrected value for the pulse wave velocity includes determining a difference between the value for the pulse wave velocity and the value for the flow velocity.

16. The method of claim 9, where the value for blood density of the subject is an estimate of blood density based on values for blood density associated with a population having characteristics similar to that of the subject.

17. A noninvasive method for determining arterial distensibility of a subject under stationary conditions comprising:
providing one of an arterial diameter or radius associated with a first pressure by:
capturing, using a scanner, a first ultrasound image of an arterial segment or segments of the subject, the first ultrasound being associated with the first pressure; and
analyzing the first ultrasound image to determine the one of the arterial diameter or radius associated with the first pressure;
providing one of an arterial diameter or radius associated with a second pressure by:
capturing, using a scanner, a second ultrasound image of the arterial segment or segments of the subject, the second ultrasound image being associated with the second pressure; and
analyzing the second ultrasound image to determine the one of the arterial diameter or radius associated with the second pressure;
calculating an arterial distensibility by finding the difference between the first pressure arterial radius and the second pressure arterial radius, dividing by the difference of the product of the first pressure and the first radius and the product of the second pressure and the second radius, and multiplying by two; and
identifying vascular changes in the subject based at least on the arterial distensibility to determine when the subject has increased cardiovascular risk.

18. The method of claim 17, wherein the first pressure is a systolic pressure, and the second pressure is a diastolic pressure.

19. The method of claim 18, further comprising measuring the systolic pressure and the diastolic pressure.

20. The method of claim 18, further comprising estimating the systolic pressure and the diastolic pressure based on values for the systolic pressure and the diastolic pressure associated with a population having characteristics similar to that of the subject.

* * * * *